(12) United States Patent
Tilse

(10) Patent No.: US 7,014,462 B1
(45) Date of Patent: Mar. 21, 2006

(54) METHOD AND INSTRUMENT FOR INTRODUCING A DENTAL SYNTHETIC RESIN INTO A TOOTH CAVITY

(76) Inventor: Rainer Tilse, Bahnhofstrasse 2, D-75172 Pforzheim (DE)

(*) Notice: Subject to any disclaimer, the term of this patent is extended or adjusted under 35 U.S.C. 154(b) by 161 days.

(21) Appl. No.: 10/069,949

(22) PCT Filed: Sep. 7, 2000

(86) PCT No.: PCT/EP00/08723

§ 371 (c)(1),
(2), (4) Date: Mar. 7, 2002

(87) PCT Pub. No.: WO01/17454

PCT Pub. Date: Mar. 15, 2001

(30) Foreign Application Priority Data

Sep. 9, 1999 (DE) ............... 199 43 217
Jan. 15, 2000 (DE) ............... 100 01 513

(51) Int. Cl.
*A61C 5/04* (2006.01)

(52) U.S. Cl. .................... 433/90; 433/226

(58) Field of Classification Search ............. 433/90, 433/89, 80, 118, 119, 226, 228.1
See application file for complete search history.

(56) References Cited

U.S. PATENT DOCUMENTS

| 3,751,807 A * | 8/1973 | Noll et al. ............. 433/83 |
| 3,792,530 A * | 2/1974 | Smith ............. 433/83 |
| 3,809,977 A * | 5/1974 | Balamuth et al. ............. 318/116 |
| 3,890,713 A * | 6/1975 | Nielsen ............. 433/83 |
| 3,898,739 A * | 8/1975 | Gayso ............. 433/118 |
| 4,634,383 A | 1/1987 | Beyer et al. ............. 433/226 |
| 4,768,955 A * | 9/1988 | Hirdes ............. 433/89 |
| 4,850,875 A * | 7/1989 | Takatsu ............. 433/226 |
| 5,007,837 A * | 4/1991 | Werly ............. 433/226 |
| 5,244,933 A | 9/1993 | Eidenbenz et al. ............. 522/3 |
| 5,839,895 A * | 11/1998 | Fishburne, Jr. ............. 433/118 |

FOREIGN PATENT DOCUMENTS

| DE | 3126633 | 2/1983 |
| DE | 3403779 | 8/1985 |
| DE | 4406323 | 9/1995 |
| DE | 9638068 | 3/1998 |
| DE | 9700213 | 7/1998 |
| DE | 9806256 | 5/1999 |
| EP | 0970717 | * 9/1988 |
| FR | 2190176 | * 1/1974 |

* cited by examiner

Primary Examiner—John J Wilson
(74) Attorney, Agent, or Firm—Ladas & Parry LLP

(57) ABSTRACT

A method and a device for introducing a dental filling material with a synthetic resin base into a tooth cavity. The filling material has a viscosity which is lowered under the action of vibrations, such as when subjected to ultrasound. The device subjects the filling material to the action of vibrations as it is injected into the tooth cavity.

14 Claims, 1 Drawing Sheet

METHOD AND INSTRUMENT FOR INTRODUCING A DENTAL SYNTHETIC RESIN INTO A TOOTH CAVITY

Since the time tooth fillings made from amalgam have first been discussed because of fears that the mercury contained in them might lead to health problems, an ever increasing number of tooth fillings made from plastic materials have been used. These fillings are made from filling compounds on a synthetic resin basis. It has been known to select as synthetic resin basis a synthetic resin that can be hardened by ultraviolet light, and to embed into that synthetic resin an inorganic powder or a mixture of different inorganic powders as fillers. The higher the proportion of the filler in the filling compound, the higher is the viscosity of the compound, and the lower is the degree of shrinkage during hardening. When preparing direct tooth fillings, it is however difficult to introduce highly viscous, pasty filling compounds into the cavity of the tooth to be filled in such a way that the latter will be filled completely, and this especially in the case of narrow long cavities. The dentist has no means of knowing with certainty in this case if the filling compound has been brought down to the bottom of the cavity and if it fills the cavity completely. If direct fillings are prepared using filling compounds which contain a smaller proportion of filler and which, therefore, are less viscous, then it is of course possible to directly fill even narrow and deep cavities, but such filling compounds, that contain a smaller proportion of fillers, shrink more heavily when hardening, and this may give rise to gaps between the filling and the tooth and cracks in the filling which will cause damage to the tooth later. Low-viscous filling compounds are connected with the further disadvantage that until hardened they can be retained in the cavity to be filled with difficulty only and that there is a risk that parts of the filling compound may flow out of the cavity, deposit in undesirable areas of the crown, and/or penetrate into pockets between the dental neck and the gums. Due to the higher degree of shrinkage of the thinner filling compounds it is further difficult to achieve a filling with a surface that ends exactly flush with the surface of the crown in the environment of the cavity. Although filling compounds with a higher proportion of inorganic fillers provide the advantage that they shrink less heavily and that they are more abrasion-resistant, they can be filled into a cavity only with greater difficulty.

For filling a filling compound into a cavity of a tooth, there have been available hand-held devices in the form of guns or syringes with small supply containers in the form of cartridges placed therein. By pressing a lever, the filling compound is extruded through a nozzle configured as a small tube. The small tube is introduced into the cavity, or is placed on the latter's edge, in order to fill the cavity.

It has also been known to prepare indirect fillings with a resin-based filling compound. In the case of indirect fillings, an inlay consisting of a plastic or ceramic material, which has been prefabricated by a dental technician, is bonded in a cavity managed in the occlusion surface of a molar tooth using the resin-based filling compound. If the filling compound used for this purpose is one that flows easily it is a problem that when pressing down the inlay any superfluous compound will be squeezed out laterally and will run down along the crown of the tooth and into pockets in the gums. In addition, the material shrinks as it cures, and this shrinkage may lead to the disadvantageous formation of cracks and gaps that has been described before. If, on the other hand, the filling compound used for preparing an indirect filling is one that exhibits a higher viscosity, containing a higher proportion of fillers, then there is no risk that the filling compound may run down along the crown of the tooth, but the highly viscous, pasty filling compound will to some degree resist spreading in the cavity between the tooth and the inlay when the latter is being pressed down. A certain progress has been achieved by a technique where the dentist employs a handpiece of the kind normally used for cleaning the teeth by means of ultrasound, for acting upon the inlay from the outside. The handpiece carries on its tip a detachable cleaning tool. The dentist removes that tool and replaces it by a special end piece onto which the ultrasonic oscillations are transmitted. The dentist presses the end piece onto the inlay. The action of the ultrasound reduces the viscosity of the filling compound so that it will spread more easily in the cavity under the inlay. The action of the ultrasound must be applied in several steps, with pauses between such steps, in order to prevent the filling compound from curing prematurely due to the heating-up effect produced by the ultrasound. This way of proceeding is limited to the preparation of indirect fillings because an inlay is required to permit the ultrasonic oscillations to be transmitted to the filling compound already present in the cavity.

Now, it is the object of the present invention to simplify the preparation of direct tooth fillings using filling compounds on the basis of synthetic resin, and to reduce or even fully overcome the disadvantages described before such as, especially, filling deficiencies, formation of cracks and the risk of filling compound escaping from the cavity.

This object is achieved by a method having the features defined in claim 1 and a hand-held device having the features defined in claim 3. Advantageous further developments of the invention are the subject of the dependent claims.

According to the invention, one acts upon the filling compound with sound of a frequency high enough to reduce the viscosity of the filling compound, especially with ultrasound, not only after the filling compound has been filled into a cavity, but already during the operation of filling the filling compound into the cavity. This was not possible heretofore in the first line because a suitable tool was not available for this purpose.

The invention provides considerable advantages:

It can be employed for the preparation of direct fillings using highly viscous, pasty filling compounds that contain a high proportion of inorganic fillers. The filling compound, which initially is highly viscous and pasty, is caused to flow more easily during the filling-in process under the action of sound, especially ultrasound, and this in spite of the high content of fillers.

It is thus possible to use for the normally highly viscous, pasty filling compound a narrow nozzle, especially in the form of a short and narrow small tube of the kind which under normal conditions can be used only for low-viscosity filling compounds.

A narrow nozzle, especially in the form of a narrow small tube, allows without any problem the filling compound to be brought down to the very bottom of the cavity to be filled, and the cavity to be filled completely.

Since the filling compound is subjected to the action of sound, especially ultrasound, as it flows through the nozzle, the filling compound will not heat up very much even when it is subjected to the action of sound continuously so that the cavity can be filled without any interruption.

Once the filling compound has left the nozzle, the action of the sound on the compound diminishes rapidly, and the filling compound assumes once more its highly viscous, pasty state. Accordingly, there is no longer a risk, not even with cavities that are open at the bottom, that the filling compound may flow out of the cavity.

The invention facilitates and accelerates the dentist's work quite considerably.

It is easily possible to prepare a direct filling that ends flush with the tooth surface surrounding the cavity.

Due to the high proportion of inorganic fillers, especially powdered quartz, no gaps and cracks will form during hardening; the filling is wear-resistant and capable of closing the cavity permanently.

Although the invention is especially well suited for direct fillings, it is suitable also for indirect fillings where it facilitates the determination of the correct quantity of filling compound needed and largely prevents the filling compound from flowing over as the inlay is pressed down.

Especially suited for filling a filling compound on synthetic resin basis into a cavity of a tooth is a hand-held device which takes the initially highly viscous, pasty filling compound from a supply container and which is provided with a nozzle from which the filling compound is then dispensed. The hand-held device comprises a sound generator, especially an ultrasound generator, that sets the nozzle into oscillation which oscillation is then transmitted to the filling compound as the latter flows through the nozzle. In addition, the hand-held device comprises a handle portion so that it can be handled by the dentist, and further means for conveying the filling compound out of the supply container and into the nozzle. This means may consist of a small piston pump by which the filling compound is pushed out of the supply container. There is, however, also the possibility to press the filling compound out of the supply container manually. In cases where the supply container is configured as small cartridge, the filling compound can be pressed out by means of a piston which can be operated manually using a lever or a push button. In cases where the supply container is configured as a tube or a flexible hose, a squeezing means may be provided in the hand-held device for pressing out the filling compound by manual operation. The hand-held device can be configured in the way of a spray gun and may be provided with a lever which can be operated by the index finger, just as the firing lever of a pistol, and which allows the filling compound to be finely metered. But there is also the possibility to configure the hand-held device similar to a dentist's handpiece and to provide it, for example, with a lateral lever or push button of the kind known in connection with handpieces employed for the supply of compressed air and spray water, handling of which is well-known to any dentist so that he/she will be capable, without any difficulty, to employ the same handling technique also for the metered application of the filling compound.

Preferably, the lever or push button by which the process of conveying the filling compound is actuated, is simultaneously used as actuating element for the ultrasound generator so that by actuating a common actuating element the ultrasound generator and the conveying process will both be switched on. As soon as the actuating element is released, the conveying process stops and the ultrasound generator is switched off. This guarantees extremely comfortable handling for the dentist.

A piezoelectric oscillator is especially well-suited as an ultrasound generator because it is available in particularly small overall sizes. The use of a magnetostrictive oscillator or of an oscillator that is excited pneumatically is also possible.

Preferably, the nozzle sits exchangeably in the holder of the hand-held device so that it can be exchanged after every operation. The sound generator is then coupled to the nozzle holder in oscillation-transmitting fashion so that the oscillations are transmitted to the holder, from the holder to the nozzle and from the nozzle to the filling compound. Suited nozzles are short, narrow tubes that can be discarded after every operation for reasons of hygiene so that there is no need to clean them from gradually curing plastic material.

The invention is suited for all kinds of filling compound based on synthetic resin, the viscosity of which can be temporarily reduced by the action of sound, especially the action of ultrasound of sufficiently high frequency. Such a behaviour is found with dispersions—a synthetic-resin compound filled with an inorganic filler is such a dispersion—which show thixotropic behaviour. The filling compound produced by Vivadent Ets. in FL 9494 Schaan (Liechtenstein) and sold under the trade name Tetric, which contains a mixture of UDMA ([2,2(4), 4-trimethyl hexamethylene-bis-(2-carbamoyloxyethyl)] dimethacrylate), bis-GMA (isopropylidene-bis [2 (3)-hydroxy-3(2)-(4-phenoxy)propyl]-bis(methacrylate) and TEGDMA (triethylene glycol dimethacrylate) as well as 62 percent by volume of inorganic fillers with a particle size of between 0.04 $\mu$m and 3 $\mu$m may serve as an example. A mixture of silanised silicon dioxide, silanised barium glass filler and ytterbium (III)-fluoride is provided as filler. In addition to such composites, glass ionomer cements, compomers and ormoceres may also be used.

One embodiment of the invention is shown diagrammatically in the attached drawing in which.

Figure 1:
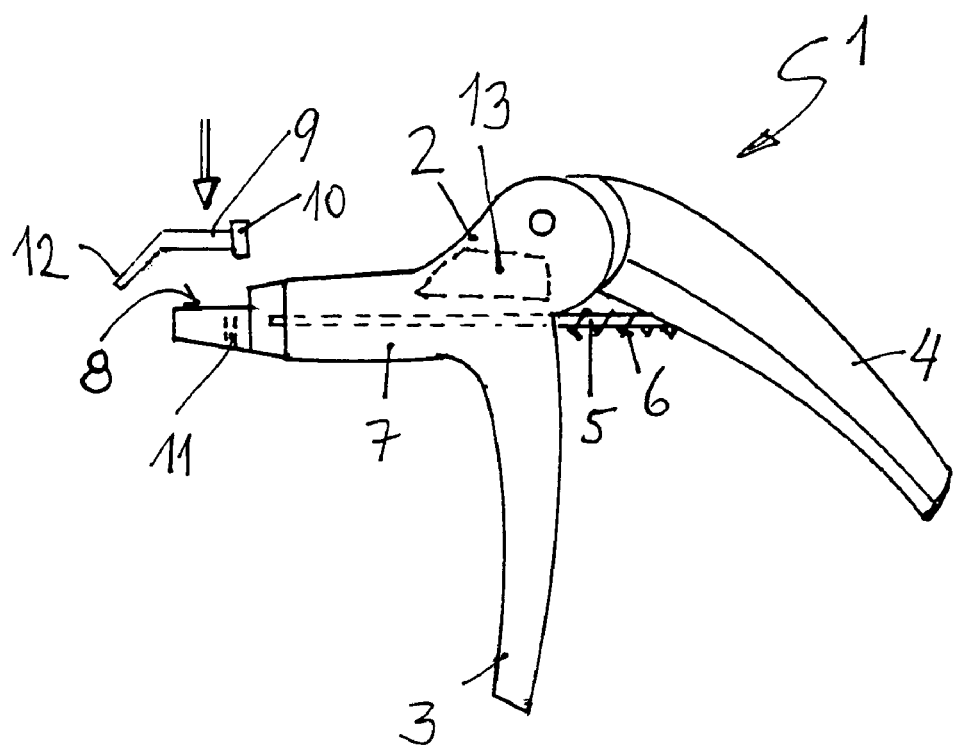
FIG. 1 shows a side view of an applicator.
Figure 2:
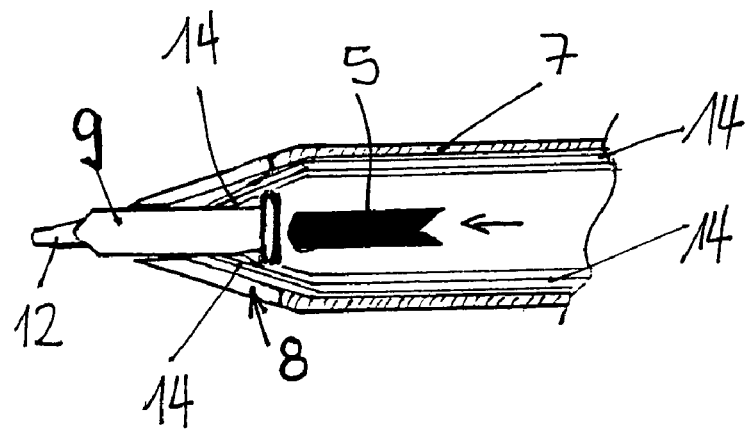
FIG. 2 shows a top view, sectioned in part, of the front portion of the applicator as a detail.

The drawing shows an applicator 1 comprising a holding portion 2, a handle 3 and a lever 4 which is pivotally mounted on the holding portion 2 and which acts on a plunger 5 surrounded by a return spring 6, which latter is mounted between the holding portion 2 and the lever 4 for returning the lever 4 to its original position after it has been actuated.

The holding portion 2 comprises a tapering tube portion 7 with a recess 8 cut into its jacket at the forward pointed end so that a cartridge 9 can be inserted into the recess from the side. The cartridge 9 is provided with a flange 10 that abuts against a stop 11 provided in the tube portion 7.

The cartridge 9 contains a filling compound that can be pressed out through an angled nozzle 12. This is achieved by the plunger 5 which acts upon the rear end of the cartridge 9 when the dentist's hand urges the lever 4 against the handle 3.

The rear portion of the holding element 2 contains an ultrasound oscillator 13 operating especially on a piezoelectric basis. The ultrasound oscillator 13 is connected with the cartridge 9 by lamellas 14 extending longitudinally in the tube portion 7. Coupled with the lever 4 is an electric switch for switching the ultrasound oscillator on and off so that the ultrasound oscillator 13 is switched on when the lever 4 is actuated, and is switched off when the lever 4 is returned to its original position.

What is claimed is:

1. Hand-held device for filling a cavity of a tooth, the device comprising:
   a supply container:
   a synthetic resin filling compound contained in said supply container and having a viscosity which is lowered under the action of vibrations;

means for conveying the filling compound from said supply container to a nozzle, from which the filling compound is injected into said cavity;

a handle portion; and a sound generator connected to the nozzle;

wherein the sound generator sets the nozzle into oscillation while the filling compound is conveyed from the supply container to the nozzle, and the oscillation if the nozzle is transmitted to the filling compound as the filling compound flows through the nozzle.

2. The hand-held device as defined in claim 1, wherein the container is a cartridge which is provided with the nozzle.

3. The hand-held device as defined in claim 2, wherein the sound generator is connected to the cartridge.

4. The hand-held device as defined in claim 1, wherein the hand-held device is configured in the way of a dentist's handpiece.

5. The hand-held device as defined in claim 1, wherein the nozzle is a short small tube.

6. The hand-held device as defined in claim 1, wherein the sound generator comprises a piezoelectric oscillator.

7. The hand-held device as defined in claim 1, wherein the sound generator comprises a magnetostrictive oscillator.

8. The hand-held device as defined in claim 1, wherein the sound generator comprises a pneumatically excited oscillator.

9. The hand-held device as defined in claim 1, wherein the hand-held device is configured in the way of a spray gun.

10. The hand-held device as defined in claim 1, wherein said actuating element comprises a lever or a push button.

11. The hand-held device as defined in claim 1, wherein said sound generator is an ultrasound generator.

12. A method for filling a filling material comprising the steps of:

providing a synthetic resin having a viscosity which is lowered under the action of vibrations, and injecting said synthetic resin into a cavity of a tooth while subjecting the synthetic resin to the action of sound.

13. The method as defined in claim 12, wherein the synthetic resin is injected into the cavity using a nozzle, and the nozzle is subjected to the action of sound.

14. The method as defined in claim 12, wherein the synthetic resin is subjected to ultrasound.

* * * * *